US010195251B2

(12) United States Patent
Wen

(10) Patent No.: US 10,195,251 B2
(45) Date of Patent: Feb. 5, 2019

(54) METHODS OF TREATMENT FOR RETINAL DISEASES USING MANF AND CNDF

(71) Applicant: Rong Wen, Miami, FL (US)

(72) Inventor: Rong Wen, Miami, FL (US)

(73) Assignee: UNIVERSITY OF MIAMI, Miami, FL (US)

(*) Notice: Subject to any disclaimer, the term of this patent is extended or adjusted under 35 U.S.C. 154(b) by 0 days.

(21) Appl. No.: 15/436,050

(22) Filed: Feb. 17, 2017

(65) Prior Publication Data
US 2018/0028607 A1 Feb. 1, 2018

Related U.S. Application Data

(63) Continuation of application No. 14/124,802, filed as application No. PCT/US2012/041701 on Jun. 8, 2012.

(60) Provisional application No. 61/495,182, filed on Jun. 9, 2011.

(51) Int. Cl.
A61K 38/00 (2006.01)
A61K 49/00 (2006.01)
A61B 5/00 (2006.01)
C07K 14/00 (2006.01)
G01N 33/53 (2006.01)
A61K 38/18 (2006.01)
C07K 14/475 (2006.01)
C07K 14/48 (2006.01)

(52) U.S. Cl.
CPC ............ *A61K 38/18* (2013.01); *C07K 14/475* (2013.01)

(58) Field of Classification Search
CPC .. A61K 38/18; A61K 2300/00; A61K 38/185; A61K 48/00; A61K 35/30; A61K 38/00; A61K 38/1709; C07K 14/475; C07K 14/4756; C07K 14/48; C07K 2319/02; G01N 33/573
See application file for complete search history.

(56) References Cited

U.S. PATENT DOCUMENTS

| 4,612,012 | A | 9/1986 | White | |
| 6,106,552 | A | 8/2000 | Lacombe et al. | |
| 7,452,969 | B2* | 11/2008 | Saarma | C07K 14/475 435/320.1 |
| 8,084,425 | B2* | 12/2011 | Commissiong | C07K 14/475 424/570 |
| 2002/0132978 | A1* | 9/2002 | Gerber | C07K 14/47 530/350 |
| 2002/0182198 | A1* | 12/2002 | Commissiong | C07K 14/475 424/94.1 |
| 2004/0243159 | A1 | 12/2004 | Shiuey | |
| 2005/0177231 | A1 | 8/2005 | Ricci et al. | |
| 2005/0255114 | A1 | 11/2005 | Labat et al. | |
| 2006/0057582 | A1 | 3/2006 | Rosen et al. | |
| 2006/0084619 | A1* | 4/2006 | Saarma | C07K 14/475 514/44 R |
| 2006/0195915 | A1* | 8/2006 | Saarma | C07K 14/475 800/8 |
| 2006/0216289 | A1* | 9/2006 | de Sauvage | C07K 14/71 424/143.1 |
| 2008/0269154 | A1* | 10/2008 | Saarma | C07K 14/475 514/44 R |
| 2008/0305083 | A1 | 12/2008 | Dorey et al. | |
| 2009/0041759 | A1 | 2/2009 | McVey et al. | |
| 2009/0133247 | A1* | 5/2009 | Meyers | H01L 23/5387 29/729 |
| 2009/0196854 | A1* | 8/2009 | Clark | A61K 48/0008 424/93.2 |
| 2009/0282495 | A1* | 11/2009 | Saarma | C07K 14/475 800/13 |
| 2010/0069915 | A1 | 3/2010 | Shiuey | |
| 2010/0119491 | A1* | 5/2010 | Commissiong | C07K 14/475 424/93.7 |
| 2010/0185281 | A1 | 7/2010 | Daphna | |
| 2010/0285045 | A1* | 11/2010 | Saarma | C07K 14/475 424/185.1 |
| 2011/0152967 | A1* | 6/2011 | Simon | A61N 1/40 607/45 |
| 2011/0251132 | A1* | 10/2011 | Saarma | C07K 14/475 514/17.8 |
| 2013/0078220 | A1* | 3/2013 | Commissiong | C07K 14/475 424/93.7 |
| 2013/0274186 | A1* | 10/2013 | Runeberg-Roos | C07K 14/48 514/6.9 |

(Continued)

FOREIGN PATENT DOCUMENTS

| JP | 2004528835 | 9/2004 |
| JP | 2014518204 | 7/2014 |

(Continued)

OTHER PUBLICATIONS

Medeiros et al. Invest. Ophthalmol. Vis. Sci. 2001; 42:795-803.*
Petrova et al. J. Mol. Neurosci. 2003; 20:173-88.*
Tao, W., Wen, R., Aguirre, G.D., Laties, A.M. (2006). Cell-Based delivery systems: development of encapsulated cell technology for ophthalmic applications. In G.J. Jaffe, P. Ashton (Eds.), Intraocular drug delivery: principles and clinical applications (Ch. 8). Taylor & Francis.

(Continued)

*Primary Examiner* — Chang-Yu Wang
(74) *Attorney, Agent, or Firm* — Malloy & Malloy, PL

(57) ABSTRACT

The present invention provides methods of treating a retinal disorder comprising administering an effective amount of a neurotrophic factor to a subject having the retinal disorder. The neurotrophic factors useful in the invention include mesencephalic astrocyte-derived neurotrophic factor (MANF) and conserved dopamine neurotrophic factor (CDNF). The present invention further comprises pharmaceutical compositions and kits containing MANF and CDNF.

31 Claims, 9 Drawing Sheets

Specification includes a Sequence Listing.

(56) References Cited

U.S. PATENT DOCUMENTS

| | | | | |
|---|---|---|---|---|
| 2013/0315962 | A1* | 11/2013 | Garcia-Bennett | A61K 9/5115 424/400 |
| 2014/0094413 | A1* | 4/2014 | Harding | A61K 38/05 514/17.7 |
| 2014/0243264 | A1 | 8/2014 | Wen | |

FOREIGN PATENT DOCUMENTS

| | | | | |
|---|---|---|---|---|
| WO | WO200170174 | * | 9/2001 | |
| WO | 0185083 | A1 | 11/2001 | |
| WO | 2009120810 | A2 | 10/2009 | |
| WO | 2009133247 | A1 | 11/2009 | |
| WO | WO-2009133247 | A1 * | 11/2009 | C07K 14/475 |
| WO | 2011053675 | A2 | 5/2011 | |
| WO | 2012170918 | A2 | 12/2012 | |

OTHER PUBLICATIONS

Lindholm, "Novel neurotrophic factor CDNF protects and rescues midbrain dopamine neurons in vivo", Nature Publishings Group, vol. 448, pp. 73-78 (Jul. 5, 2007).

Tao, "Application of Encapsulated Cell Technology for Retinal . . . ", Ophthalmology Research: Retinal Degenerations: Biology, Diagnostics, and Therapeutics, Ch. 21, pp. 401-413.

Liu, "Activation of Caspase-3 in the Retina of Transgenic Rats with the Rhodopsin Mutation S334ter during . . . " The Journal of Neuroscience, pp. 4778-4785 (Jun. 15, 1999).

Airavaara, "Mesencephalic Astrocyte-Derived Neurotrophic Factor Reduces Ischemic Brain Injury and Promotes . . . ", The Journal of Comparative Neuroloy, 515 pp. 116-124 (2009).

Parkash, "The structure of the conserved neurotrophic factors MANF and CDNF explains why . . . ", Protein Engineering, Design & Selection, vol. 22, No. 4, pp. 233-241 (Jan. 10, 2009).

Tadimalla, "Mesencephalic Astrocyte-Derived Neurotrophic Factor Is an Ischemia . . . " Circulation Research, circres.ahajournals.org at Univ of Miami, pp. 1249-1258 (Apr. 11, 2011).

Sieving, "Ciliary neurotrophic factor (CNTF) for human retinal degeneration: Phase I trial of . . . ", www.pnas.org/cgi/doi/10.1073/pnas.0600236103, vol. 103, No. 10 (Mar. 7, 2006).

Parkash, "Neurotrophic factors and their receptors", Research Program in Structural Biology and Biophysics, Institute of Biotechnology, University of Helsinki (Oct. 16, 2009)

Xiang, Ma, Anthology of Medicine, vol. 25, No. 2, pp. 334-336. 2006.

English Translation of Non-Patent Literature—"Xiang, Ma, Anthology of Medicine, vol. 25, No. 2, pp. 334-336. 2006."

Wen et al., "Mesencephalic Astrocyte-derived Neurotrophic Factor (MANF) Protects Rod and Cone Photoreceptors from Degeneration in Transgenic Rats Carrying the S334ter Rhodopsin Mutation" (May 7, 2012).

* cited by examiner

FIGURE 4A
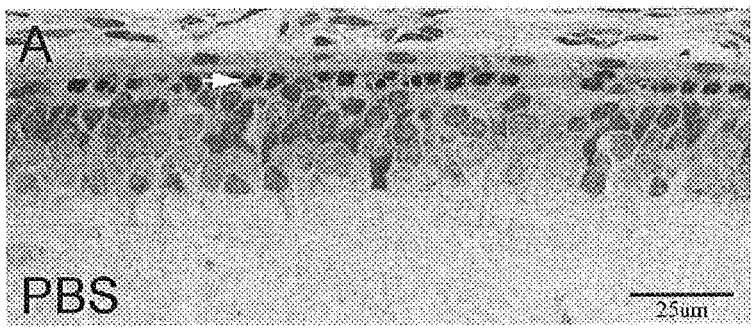
FIGURE 4B
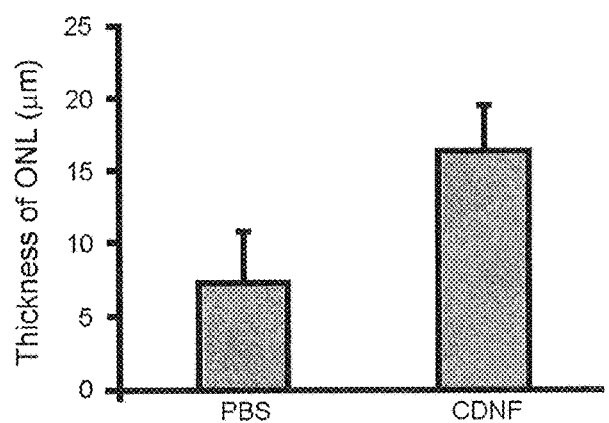
FIGURE 4C

FIGURE 5A                    FIGURE 5B

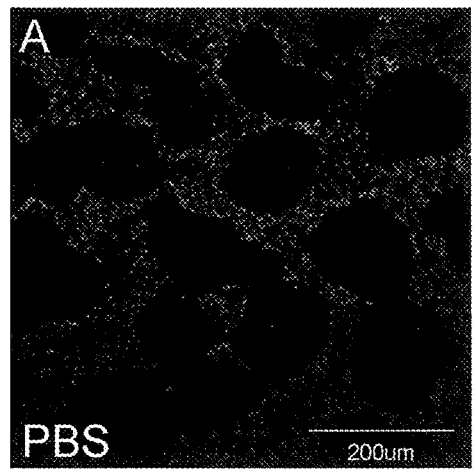
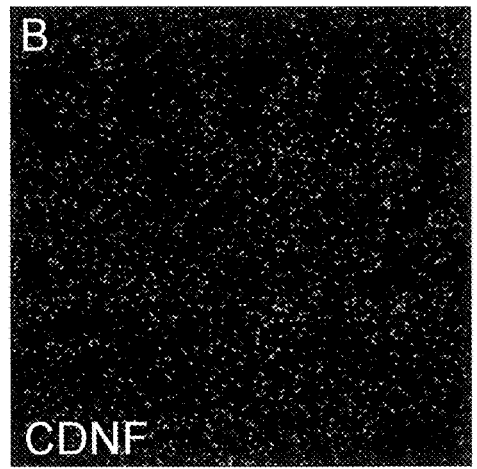
FIGURE 6A       FIGURE 6B
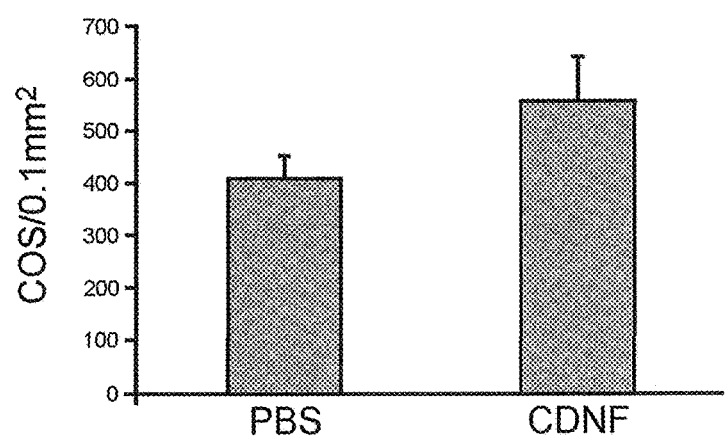
FIGURE 6C

METHODS OF TREATMENT FOR RETINAL DISEASES USING MANF AND CNDF

CROSS-REFERENCE TO RELATED APPLICATION

The present application is a continuation application of previously filed, now pending application having Ser. No. 14/124,802, filed on Apr. 11, 2014 incorporated herein by reference, which is a § 371 national phase entry of International Application No. PCT/US2012/041701, filed Jun. 8, 2012, which claims the benefit of U.S. Provisional Application Ser. No. 61/495,182, filed Jun. 9, 2011, which is incorporated herein by reference in its entirety.

STATEMENT REGARDING FEDERALLY-SPONSORED RESEARCH AND DEVELOPMENT

This invention was made with U.S. government support under grant numbers RO-1 EY-018586, R0-1 EY-015289, P30 EY-14801 awarded by the National Eye Institute, National Institutes of Health (NEI/NIH) and grant number W81XWH-09-1-0674 awarded by the United States Department of Defense. The U.S. government may have certain rights in the invention.

BACKGROUND OF THE INVENTION

Field of the Invention

This invention relates generally to the field of retinal degenerative disorders. More particularly, it concerns methods of treating retinal degenerative disorders using neurotrophic factors and compositions and kits comprising neurotrophic factors.

Description of the Related Art

Mesencephalic astrocyte-derived neurotrophic factor (MANF) and conserved dopamine neurotrophic factor (CDNF) are two known members of a novel evolutionarily conserved protein family with neurotrophic capabilities (Petrova et al., 2003; Lindholm et al., 2007). The first member of the family, MANF, was identified from the conditional medium of a rat type-1 astrocyte cell line, namely, the ventral mesencephalic cell line 1 (VMCL1), to be a factor that promotes the survival of cultured embryonic dopaminergic neurons (Petrova et al., 2003). MANF also significantly reduces infarction in the ischemic cortex in a rat model of stroke (Airavaara et al., 2009) and promotes the survival of cultured heart muscle cells (Tadimalla et al., 2008). CDNF, on the other hand, was first identified in silico and then biochemically characterized (Lindholm et al., 2007). It was expressed in murine and human tissues, including the brain. A single injection of CDNF rescues amphetamine-induced loss of dopaminergic neurons in the substantia nigra (Lindholm et al., 2007). Structural analysis showed that both MANF and CDNF have an N-terminal saposin-like lipid-binding domain and a C-terminal domain that may be responsible for the endoplasmic reticulum (ER) stress response, and neither protein resembles any known growth factor (Parkash et al., 2009). The receptors and signaling pathways of CDNF and MANF are unknown. While these two proteins have been considered to be potential treatments for Parkinson's disease, the inventor herein has considered them to be potential treatments for other neurodegenerative disorders, including retinal degenerative disorders, such as inherited retinal disorders, age-related macular degeneration, and glaucoma.

SUMMARY OF THE INVENTION

In light of their neurotrophic capabilities and treatment potential in neurodegenerative disorders, the present invention discloses the neurotrophic factors, MANF and CDNF, being used to rescue photoreceptors and retinal ganglion cells in retinal degenerative disorders in patients, including inherited retinal disorders, age-related macular degeneration, and glaucoma.

Specifically, the present invention provides a method of treating a retinal disorder comprising administering an effective amount of a neurotrophic factor to a subject having the retinal disorder. The subject in need of treatment may be an animal, which may include a mammal (e.g., a human). The retinal disorders amenable to treatment or suppression by the methods of the invention comprise neurodegenerative disorders, such as age-related macular degeneration, glaucoma, inherited retinal disorders, sporadic retinal disorders, other degenerative retinal disorders, or retinal injuries.

The neurotrophic factors that may be administered in the embodiments of the present invention include MANF and CDNF, individually or in combination. The neurotrophic factor may be a recombinant or isolated factor, and in particularly useful embodiments, the neurotrophic factor is a human neurotrophic factor.

In particular embodiments, the neurotrophic factor is administered in a pharmaceutically acceptable vehicle. In some embodiments, the neurotrophic factor is injected into an eye of a subject in need thereof, which may also be administered using a sustained-releasing vehicle.

The present invention also provides a method for promoting neuroprotection in a neuronal cell comprising contacting the neuronal cell with a neurotrophic factor, which may include the neurotrophic factors MANF and CDNF, either individually or in combination. The contacting of neuronal cells can take place in vitro or in vivo.

The cell types amenable to treatment by the methods of the invention comprise ganglion cells or photoreceptor cells.

The present invention also provides a pharmaceutical composition comprising a neurotrophic factor, which may include MANF and CDNF, individually or in combination. The present invention is also directed to kits of parts comprising neurotrophic factors, reagents, and instructions for use thereof. Furthermore, the present invention may utilize neurotrophic factors having the sequences of SEQ ID NOS: 1, 2, 3, or 4.

The methods, compositions and kits herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures in which:

FIG. 3A shows the control, PBS (Phosphate-Buffered Saline) treated retina. FIG. 3B is representative of a MANF-treated retina. Scale bar, 25 μm. FIG. 3C is a graphical representation of the quantitative analysis of the thickness of the outer nuclear layer of the retina in PBS treated and MANF treated retinas.

FIGS. 4A-4C show light microscopy photographs of sections of the outer nuclear layers of the retina in control- and CDNF-treated S334ter3 rats, as well as quantitative analysis of the thickness of the outer nuclear layer in each. FIG. 4A is representative of control PBS (Phosphate-Buffered Saline) treated retinas. FIG. 4B is representative of CDNF-treated retinas. Scale bar, 25 μm. FIG. 4C is a graphical representation of the quantitative analysis of the thickness of the outer nuclear layer of the retina in PBS-treated and CDNF-treated retinas.

FIGS. 5A-5C show fluorescent microscopy photographs of cone outer segment (COS) of whole mounted retinas stained with Alexa Fluor 488 conjugated PNA (peanut agglutinin) in control- and MANF-treated S334ter3 rats (FIGS. 5A and 5B), as well as quantitative analysis of each (FIG. 5C). FIG. 5A is representative of a control, PBS-treated retina. FIG. 5B is representative of a MANF-treated retina. Scale bar, 50 μm. FIG. 5C is a graphical representation of the quantitative analysis of the number of labeled cells of the retina in PBS-treated and MANF-treated retinas.

FIGS. 6A-6C show fluorescent microscopy photographs of COS of whole mounted retinas stained with Alexa Fluor 488 conjugated PNA in control- and CDNF-treated S334ter3 rats (FIGS. 6A and 6B), as well as quantitative analysis of each (FIG. 6C). FIG. 6A is representative of a control PBS-treated retina. FIG. 6B is representative of a CDNF-treated retina. FIG. 6C is a graphical representation of the quantitative analysis of the number of labeled cells of the retina in PBS-treated and CDNF-treated retinas.

FIG. 7A is representative of control retinal ganglion cells experiencing no optic nerve crush. FIG. 7B is representative of retinal ganglion cells two weeks after optic nerve crush and PBS treatment. FIG. 7C is representative of retinal ganglion cells two weeks after optic nerve crush and MANF treatment.

Like reference numerals refer to like parts throughout the several views of the drawings.

DETAILED DESCRIPTION OF THE PREFERRED EMBODIMENT

Figure 1:
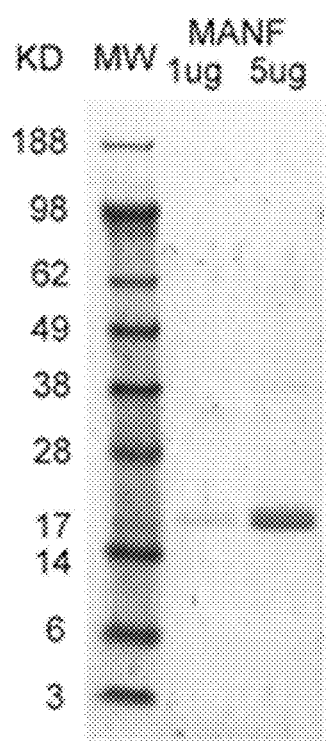
FIG. 1 shows a photograph of gel electrophoresis of purified recombinant human MANF protein, at 1 μg and 5 μg amounts, compared to a standard molecular weight (MW) ladder showing the size of purified MANF protein as approximately 20 kilodaltons (KD).

The present invention is directed to methods of treatment, compositions and kits for treating retinal disorders.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

All genes and gene products (including RNA and proteins), and their respective names, disclosed herein are intended to correspond to homologs from any species for which the compositions and methods disclosed herein are applicable. When a gene or gene product from a particular species is disclosed, it is understood that this disclosure is intended to be exemplary only and is not to be interpreted as a limitation unless the context in which it appears clearly indicates otherwise. For example, the genes and gene products disclosed herein, which in some embodiments relate to mammalian (including human) nucleic acid and/or amino acid sequences, are intended to encompass homologous and/or orthologous and/or paralogous genes and gene products from other animals including, but not limited to, other mammals, fish, reptiles, amphibians, birds, and other vertebrates.

In the context of the present invention, the terms "polypeptide" and "protein" are equivalent and mutually interchangeable. They refer to any amino acid chain, and include any post-translational modifications thereto (for example phosphorylation or glycosylation).

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject. Furthermore, transgenic animals (e.g., transgenic rats and mice) are useful in the methods of the present invention.

As used herein, the term "compound" refers to a neurotrophic factor, unless clearly indicated otherwise. The neurotrophic factor can be represented, described, and/or applied for the purposes of the present invention in recombinant DNA, RNA or protein form. The neurotrophic factor can also be in an isolated form, as isolated and purified from an animal, which could also be a subject. In some embodiments, the neurotrophic factor may be a polypeptide, polynucleotide, or fragment thereof. The term "biologic" may also be used interchangeably with "compound" herein to refer to a neurotrophic factor of the present invention.

As used herein, the term "fragment" refers to a portion of a compound. For example, when referring to a protein, a fragment is a plurality of consecutive amino acids comprising less than the entire length of the polypeptide. For instance, a fragment of a compound can share up to 99%, 95%, 90%, 85%, 80%, 75%, 70%, 65%, or 60% of its sequence with the parent compound.

As used herein, the term "administering" refers to providing a therapeutically effective amount of a chemical or biological compound or pharmaceutical composition to a subject, using intravitreal, intraocular, ocular, subretinal, intrathecal, intravenous, subcutaneous, transcutaneous, intracutaneous, intracranial, topical and the like administration. The chemical or biological compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; nanoparticles; and the like.

The chemical or biological compound or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravitreal delivery, intraocular delivery, ocular delivery, subretinal delivery, intrathecal delivery, intravenous delivery, subcutaneous delivery, transcutaneous delivery, intracutaneous delivery, intracranial delivery, topical delivery and the like. Moreover, the packaging material may be biologically inert or lack bioactivity, such as plastic polymers, silicone, etc. and may be processed internally by the subject without affecting the effectiveness of the neurotrophic factor packaged and/or delivered therewith.

It is also contemplated that the compounds of the present invention can be administered by way of an implantation vehicle, such as Encapsulated Cell Technology (ECT) or other similar or future-derived micro-implantation technologies. ECT is described in Tao, W. et al., 2006, Tao, W. and Wen, R., 2007 and Sieving et al., 2006, which are incorporated herein by reference. In some embodiments, the ECT vehicle may release the compounds of the present invention at the rate of about 250 ng to about 800 ng per $1 \times 10^6$ cells per day. The implanted vehicle may also be any other similar sustained-release vehicle, or the like, that is later developed.

The term "effective amount," as applied to the compound(s), biologics and pharmaceutical compositions described herein, means the quantity necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms would refer to any condition that impairs normal function. The condition may be caused by sporadic or heritable genetic abnormalities. The condition may also be caused by non-genetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms. Additionally, treatment can be applied to a subject or to a cell culture.

In accordance with at least one embodiment of the present invention, a method for treating a retinal disorder in a subject in need thereof comprises administering an effective amount of a compound as described herein to the subject. In one embodiment, this compound is a neurotrophic factor.

The term "neurotrophic factor" refers to deoxyribonucleic acids (DNA), and ribonucleic acids (RNA) and proteins derived therefrom, in addition to fragments thereof, that are responsible for the growth and survival of nerve cells during development and for the maintenance of adult nerve cells. In some embodiments of the present invention, the neurotrophic factor is Mesencephalic astrocyte-derived neurotrophic factor (MANF). In additional embodiments, the neurotrophic factor is conserved dopamine neurotrophic factor (CDNF). Also, the neurotrophic factor administered may be a combination of MANF and CDNF. As would be understood by those skilled in the art, MANF and CDNF may have homologs, orthologs and/or paralogs that would additionally be contemplated for use in the present invention.

In one embodiment of the present invention, the neurotrophic factor is a recombinant polypeptide. The recombinant polypeptide may be the recombinant MANF or CDNF protein. It is also contemplated in the present invention that recombinant MANF and/or CDNF polypeptide fragments can be used in the methods and kits described herein. It is further contemplated that recombinant MANF and/or CDNF full length DNA, cDNA or mRNA (or fragments thereof) may be utilized in the methods and kits described herein. In some embodiments, the DNA, cDNA or mRNA (or fragments thereof) may be comprised in a plasmid, vector, or the like. For example, polynucleotides, and fragments thereof, may be utilized by way of gene therapy techniques or encapsulated cell technology (ECT). Additionally, the present invention may utilize neurotrophic factors having the sequences of SEQ ID NOS: 1, 2, 3, or 4 (or fragments, recombinants, chimerics, or combinations thereof).

In the method of the present invention, the neurotrophic factor is administered with a pharmaceutically acceptable carrier or vehicle. For instance, the pharmaceutically acceptable carrier or vehicle can be a saline solution or any other vehicle contemplated herein.

In particular, in one embodiment, the neurotrophic factor is administered by way of injection. In some embodiments, the injection site is an eye of the subject and can be intraocular, intravitreal, subretinal and the like administration. In other embodiments, the neurotrophic factor is administered in an area adjacent to the eye, and may be through injection or other methods of delivery as described herein.

The neurotrophic factor may also be administered by way of implantation of a vehicle into an eye of the subject to be treated. The vehicle may be a microimplantation device, such as Encapsulated Cell Technology (ECT) or other similar or future-derived micro-implantation technologies.

The retinal disorder treated by the method of the present invention may be the result of an injury to a tissue or a cell of the central nervous system. The retinal disorder treated can also be a neurodegenerative disorder (e.g., retinitis pigmentosa). The tissue or cell that is injured or afflicted with a neurodegenerative disorder can be a ganglion cell, such as a retinal ganglion cell, or a photoreceptor cell. In some embodiments, the retinal disorder treated involves ganglion cell degeneration. Such ganglion cell degeneration may be induced by glaucoma.

The neurodegenerative disorders contemplated for the treatment as described herein can be genetic or sporadic (i.e., happening as an isolated, non-heritable event) in nature. As would be understood by those of skill in the art, neurodegenerative disorders also embrace conditions other than retinal neurodegenerative disease, and the methods, compositions and kits of the present invention are contemplated to be applicable to other such disorders. Such disorders include Alzheimer's disease, Huntington's disease, Parkinson's disease, amyotrophic lateral sclerosis, glaucoma, age-related hearing loss, progressive supranuclear palsy, mild cognitive impairment, dementia, spinocerebellar ataxias, and the like.

In at least one embodiment, the neurotrophic factor is administered at the site of injury or affliction with the neurodegenerative disorder or in an area adjacent to the site of injury or affliction. The neurotrophic factor may also be administered by way of a vehicle that releases the factor in a controlled (i.e., time and/or dose dependant) manner, for example, as in ECT, discussed previously herein.

In accordance with another embodiment of the present invention, a method for promoting neuroprotection in a neuronal cell comprises contacting the neuronal cell with a neurotrophic factor, such as MANF, CDNF or combinations thereof. As used herein, the term "neuroprotection" refers to preventing, halting, inhibiting, or slowing nerve damage, neuron deterioration, and/or death of neurons. Neuroprotection may be elicited following damage or deterioration caused by aging, genetic factors, environmental changes, physical stress or injury, endogenous or exogenous biological or chemical factors (e.g., neurotropins, vitamins, alcohol, pharmaceutical agents, ischemia and the like), stroke, or the like.

As used herein, the term "contacting" refers to actions directed to creation of a spatial relationship between the cell(s) and the neurotrophic factor(s) (or vehicle containing the neurotrophic factor(s)), provided for a predetermined and specified time and under conditions appropriate to render a desired biological response in the contacted cell(s), such as neuroprotection. The spatial relationship between the cell(s) and the neurotrophic factor(s) can include direct contact, whereby the factor elicits a response on the contacted cell's surface directly or enters the cell for further action, or indirect contact, whereby the factor elicits a response on the cell through extracellular signaling (e.g., following activation or modification of another substance which interacts with the contacted cell). As applied herein, a biological response includes a neuroprotective response or any other response by the cell(s) that causes an arrest, inhibition, reduction, or regression of a disorder of the cell(s).

In particular embodiments of the invention, contacting neuronal cells by a neurotrophic factor takes place in vitro. "In vitro" can include in cell or tissue cultures, or test tube cultures. In other embodiments, the contacting of neuronal cells takes place in vivo. "In vivo" can include animal models (e.g., transgenic animals such as mice or rats) or living subjects as defined herein, including humans. In yet other embodiments, the contacting of neuronal cells takes place ex vivo. "Ex vivo" can include intact tissues, organs or systems, or portions thereof, derived from a subject that have been isolated or extracted from their source. As used herein, the term "isolated" means that the item described is segregated or separated (physically or chemically). Something that is isolated may still be within a subject or exist outside a subject. As used herein, the term "extracted" means that the item described is removed from the subject and exists outside the subject.

In some embodiments of the invention, the neuronal cell types amenable to treatment by the methods of the invention comprise ganglion cells or photoreceptor cells. In one particular embodiment, the neuronal cell type amenable to treatment by the methods of the invention comprises retinal ganglion cells.

The neurotrophic factors of the present invention may be recombinant or isolated neurotrophic factors and may also be either a recombinant or isolated human neurotrophic factor. As used herein with regard to genes, or fragments thereof, or gene products, or fragments thereof, the term "isolated" is defined as being removed from cells of an animal and/or purified for use in the methods described. As used herein, the term "gene" refers to a polynucleotide derived from a chromosome that codes for RNA and proteins. A gene, as used herein, may or may not include all introns, exons, promoter regions, non-coding regions, and the like, that are associated with the specific gene.

The present invention is also directed to a pharmaceutical composition or medicament comprising a neurotrophic factor, such as MANF, CDNF or combinations thereof. The pharmaceutical composition can also include other pharmaceutically acceptable compounds, excipients, additives, fillers, binders, adjuvants, or carriers or vehicles selected based upon the chosen route of administration and standard pharmaceutical practice. As such, the neurotrophic factor(s) may be used in the manufacture or preparation of medicaments and pharmaceutical compositions. Also, the medicaments and pharmaceutical compositions comprising the neurotrophic factors described may be used for the treatment of disorders as described herein.

The present invention is also directed to a kit of parts comprising neurotrophic factor(s) and other reagents needed to perform the method(s) of the present invention. The kit of parts can also include instructions for use. The neurotrophic factor(s) and reagents can be included in one or more compositions, and each neurotrophic factor and reagent can be in a composition in combination with a suitable vehicle, or can be present independently. The kit of parts may include MANF, CDNF, or combinations thereof, as purified proteins (recombinant or isolated from an animal) or as purified polynucleotides (recombinant or isolated from an animal).

In other embodiments, the kit of parts includes labeled biomarkers specific to particular neural cell types, such as photoreceptor biomarkers or retinal ganglion cell biomarkers, reference standards, and additional components that would be identifiable by those skilled in the art upon reading the present disclosure.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicant does not admit any particular reference is "prior art" to their invention.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicant does not seek to be bound by the theory presented.

The following material and methods were used for all the methods and compositions exemplified herein.

Cloning of Recombinant Human MANF and CDNF Proteins:

The open reading frames (ORF) of MANF (SEQ ID NO: 1) and CDNF (SEQ ID NO: 2) were each cloned by polymerase chain reaction (PCR) from human brain cDNAs, and resulting cloned sequences were confirmed. Each ORF was subcloned into the expression vector pQE30 (Qiagen, Valencia, Calif.), containing a 6×His-tag coding sequence to the N-terminus in frame. Next, the expression vectors containing each of MANF and CDNF sequences were expressed in *E. coli* (XL-blue, Stratagene, La Jolla, Calif.), and the corresponding expressed proteins were purified by immobilized-metal affinity chromatography on Ni-NTA Agarose columns (Qiagen) under native conditions. The eluted protein was buffer-exchanged to phosphate-buffered saline (PBS) and stored at −80° C. in small aliquots until use. The appropriate human MANF protein sequence is represented by SEQ ID NO: 3, and the appropriate human CDNF protein sequence is represented by SEQ ID NO: 4.

Visualization of Purified MANF and CDNF Proteins:

1 µg and/or 5 µg of purified protein were electrophoresed on a 4-12% NuPAEG gel and visualized with Coomassie blue to confirm purification and proper molecular weights. Molecular weight markers (MW) were electrophoresed in a lane next to the 1 µg and/or 5 µg samples.

Transgenic Animals:

Transgenic rats carrying the murine rhodopsin mutation S334ter, known as S334ter-3 rats, were generated and utilized as previously described (Liu et al., (1999)).

Photoreceptor Protection Assay:

Single intravitreal injections of MANF and PBS (control) were given to S334ter3 rats. Specifically, 6 µg MANF was injected into one eye of a rat at postnatal day (PD) 9, and 3 µL PBS was contemporaneously injected into the remaining eye of the same rat as a control. Injections were performed through a 33-gauge needle connected to a 10 µL microsyringe (Hamilton, Reno, Nev.). Animals were sacrificed at PD21 and each eye harvested, plastic embedded, and sectioned as previously described (Liu et al., (1999)). The resulting semi-thin retinal sections were stained with toluidine blue and examined by light microscopy. Similar experiments were performed using 6 µg CDNF.

Cone Photoreceptor Outer Segment (COS) Protection Assay:

Single intravitreal injections of MANF and PBS (control) were given to S334ter3 rats. 6 µg MANF was injected into one eye of a rat at postnatal day (PD) 20, and 3 µL PBS was contemporaneously injected into the remaining eye of the same rat as a control. Injections were performed through a 33-gauge needle connected to a 10 µL microsyringe (Hamilton, Reno, Nev.). Animals were sacrificed 10 days after treatment at PD30 and each eye harvested. Whole-mounted retinas were stained with Alexa Fluor 488 conjugated PNA (peanut glutinin), which specifically binds to the outer segments of cone photoreceptors, and examined by fluorescence microscopy. Similar experiments were performed using 6 µg CDNF.

Optic Nerve Crush Assay:

Retinal ganglion cells of wild-type Sprague Dawley rats were labeled by retralabeling with Fluoro-Gold. One week after labeling, the optic nerves were crushed and immediately followed with intravitreal injection of 6 µg MANF. Two weeks after the nerve crush and treatment, the rats were sacrificed and retinas harvested. Whole-mounted retinas were examined by fluorescence microscopy.

MANF Protein Expression Analysis of Retina:

Equal amounts of protein extracts from retinas of wild-type Sprague Dawley rats at PD 1, PD 5, PD 8, PD 10, PD 12, PD 16, PD 25, PD 30, PD 40 and PD 60 were run on polyacrylamide gels, transferred to membranes and probed with antibodies for MANF and β-Actin. Structural protein, β-Actin, expression was analyzed to ensure consistent loading of protein extracts at each time-point analyzed.

Example 1: Purification of Recombinant Human Mesencephalic Astrocyte-Derived Neurotrophic Factor (MANF)

To test candidate neurotrophic factors for neuroprotective properties, recombinant human MANF and CDNF proteins were generated and purified for further experimentation. Recombinant human MANF was expressed in *E. coli*, purified, and visualized as described above in materials and methods. The results illustrated in FIG. 1 show that 1 µg and 5 µg of purified MANF are visualized as a single band of 20 kDa. Lane 1 depicts the molecular weight markers (MW); Lane 2 depicts 1 µg purified MANF; and Lane 3 depicts 5 µg purified MANF. "KD" refers to "kilodaltons."

Example 2: Purification of Recombinant Human Dopamine Neurotrophic Factor (CDNF)

Figure 2:
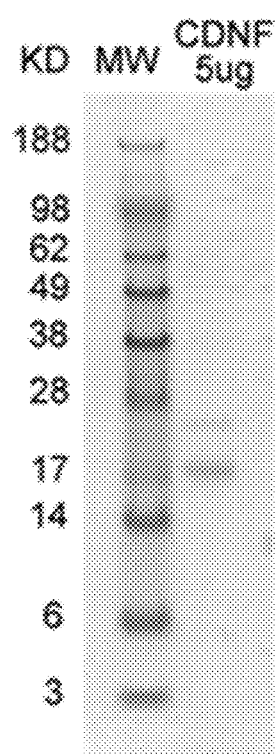
FIG. 2 shows a photograph of gel electrophoresis of purified recombinant human CDNF protein, at a 50 g amount, compared to a standard molecular weight (MW) ladder showing the size of purified CDNF protein as approximately 18 kilodaltons (KD).

CDNF was also utilized as a candidate neurotrophic factor with neuroprotective properties. Recombinant human CDNF was expressed in *E. coli*, purified, and visualized as described above in materials and methods. The results illustrated in FIG. 2 show that 5 µg of purified CDNF is visualized as a single band of 18 kDa. Lane 1 depicts the molecular weight markers (MW); Lane 2 depicts 5 µg purified CDNF. "KD" refers to "kilodaltons."

Example 3: Protection of Photoreceptors by MANF in the Retina of a Retinal Degeneration Rodent Model In search of neurotrophic factors that could rescue photoreceptors in retinal degenerative disorders, including inherited retinal disorders (e.g., retinitis pigmentosa), age-related macular degeneration, and glaucoma, recombinant human MANF protein was tested for photoreceptor protective properties in a retinal degeneration rodent model. To this end, S334ter3 transgenic rats were utilized because of their characterized progressive retinal photoreceptor degeneration (Liu et al., (1999)).

Figure 3A:
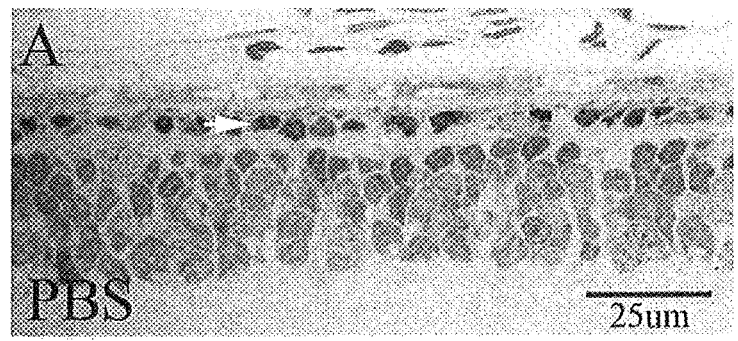
FIGS. 3A-3C show photographs of sections of the outer nuclear layers of the retina of control- and MANF-treated S334ter3 rats under light microscopy, as well as quantitative analysis of the thickness of the outer nuclear layer in each.
Figure 3B:
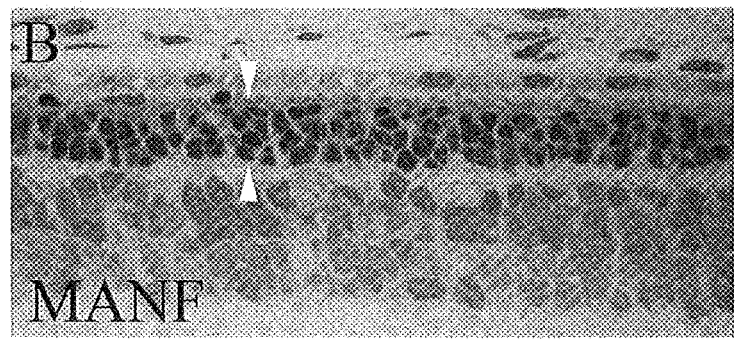

The results illustrated in FIG. 3A show that, in PBS (control) treated S334ter3 rats, the outer nuclear layer of the retina had only one row of nuclei (see arrowhead in FIG. 3A) at PD 21. The results illustrated in FIG. 3B show that a single intravitreal injection of MANF at PD 9 in the remaining eye of the same animal protected the photoreceptors from degeneration at the PD 21 time-point, as the outer nuclear layer contained three to four rows of nuclei (see between two arrowheads in FIG. 3B).

Figure 3C:
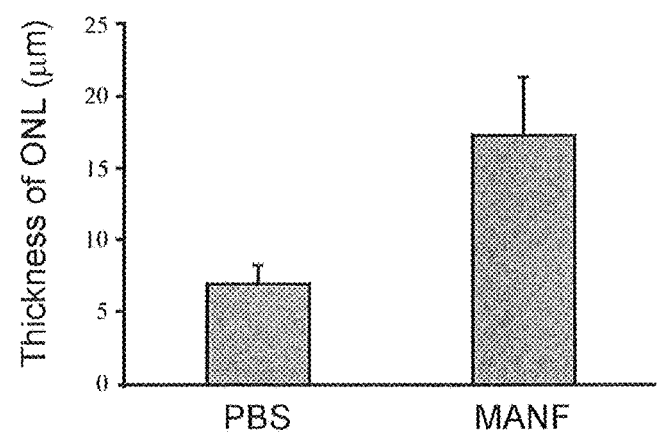

Quantitative analysis of the thickness of the outer nuclear layer of the superior retina, as shown in FIG. 3C, indicates that the outer nuclear layer of MANF treated retinas (17.47±3.96 µM, n=5) was significantly thicker than the outer nuclear layer of control PBS treated retinas (7.07±1.12 µM, n=5) (mean±SD). $P<0.001$ (student t-test).

Example 4: Protection of Photoreceptors by CDNF in the Retina of a Retinal Degeneration Rodent Model In search of other neurotrophic factors that could rescue photoreceptors in retinal degenerative disorders, recombinant human CDNF protein was tested for photoreceptor protective properties in the same retinal degeneration rodent model used for the MANF studies previously described herein.

The results illustrated in FIG. 4A show that, in PBS (control) treated S334ter3 rats, the outer nuclear layer of the retina had only one row of nuclei (see arrowhead in FIG. 4A) at PD 21. The results illustrated in FIG. 4B show that a single intravitreal injection of CDNF at PD 9 in the remaining eye of the same animal protected the photoreceptors from degeneration at the PD 21 time-point, as the outer nuclear layer contained three to four rows of nuclei (see between two arrowheads in FIG. 4B).

Quantitative analysis of the thickness of the outer nuclear layer of the superior retina, as shown in FIG. 4C, indicates that the outer nuclear layer of CDNF-treated retinas (16.61±2.87 µM, n=6) was significantly thicker than the outer nuclear layer in control PBS-treated retinas (7.4±3.43 µM, n=6) (mean±SD). $P<0.001$ (student t-test).

Example 5: Protection of the Outer Segment of Cone Photoreceptors by MANF in the Retina of a Retinal Degeneration Rodent Model As another test of photoreceptor protective abilities of neurotrophic factors, the cone outer segment was analyzed in the same retinal degeneration rodent model previously described herein following recombinant human MANF protein exposure.

The results illustrated in FIG. 5B show that a single intravitreal injection of MANF at PD 20 into the eye of the retinal degeneration rodent model protected the cone outer segment from degeneration, as measured at the PD 30 time-point, versus the remaining eye of the same animal being injected with PBS (control) (FIG. 5A).

Figure 5C:
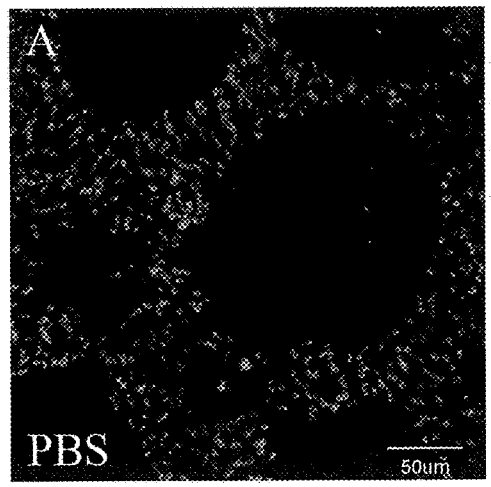
Figure 5C:
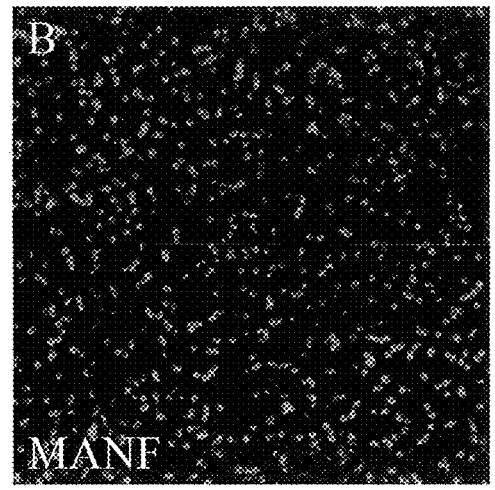
Figure 5C:
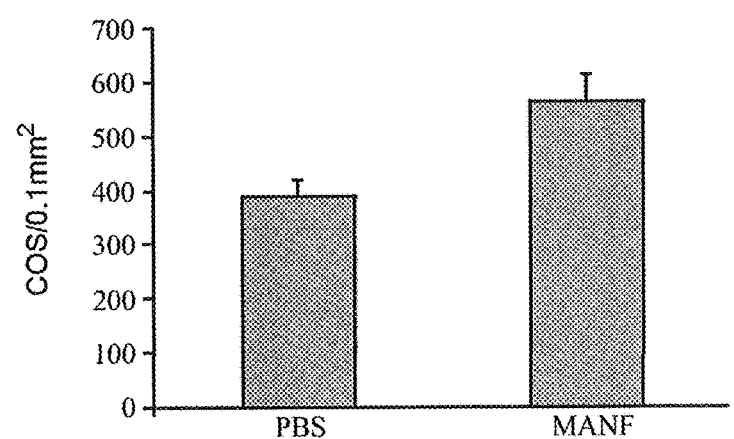

The results shown in FIG. 5C are a quantitative analysis of the number of Alexa Fluor 488 conjugated PNA-positively stained cells, indicative of the presence of cone photoreceptors. The graph indicates that MANF-treated retinas contained a significantly larger number of cone photoreceptors (569.5±46.5 µM) versus the control PBS-treated retinas (398.7±25.4 µM) (C, mean±SD). P<0.001 (student t-test).

Example 6: Protection of the Outer Segment of Cone Photoreceptors by CDNF in the Retina of a Retinal Degeneration Rodent Model The same experimental procedure in Example 5 was utilized to further test the photoreceptor protective abilities of recombinant human CDNF protein.

The results illustrated in FIG. 6B show that a single intravitreal injection of CDNF at PD 20 into the eye of the retinal degeneration rodent model protected the cone outer segment from degeneration, as measured at the PD 30 time-point, versus the remaining eye of the same animal being injected with PBS (control) (FIG. 6A).

The results shown in FIG. 6C are a quantitative analysis of the number of Alexa Fluor 488 conjugated PNA-positively stained cells, indicative of the presence of cone photoreceptors. The graph indicates that CDNF-treated retinas contained a significantly larger number of cone photoreceptors (561.5±81.3 µM) versus the control PBS-treated retinas (412.75±40.9 µM)(C, mean±SD). P=0.012 (student t-test).

Example 7: Protection of Retinal Ganglion Cells by CDNF After Optic Nerve Crush in Rats As an additional test for the neuroprotective capabilities of the neurotrophic factor MANF, retinal ganglion cells were analyzed following optic nerve crush and MANF exposure in rats.

Figure 7A:
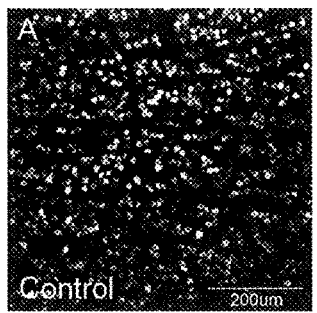
FIGS. 7A-7C show representative micrographs of Fluoro-Gold retralabeled ganglion cells of whole mounted retinas of control rats (FIG. 7A), rats after optical nerve crush in addition to PBS treatment as a control (FIG. 7B), and rats after optic nerve crush in addition to MANF-treatment (FIG. 7C).
Figure 7B:
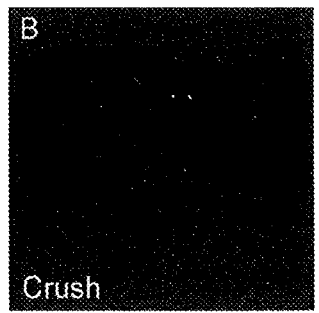
Figure 7C:
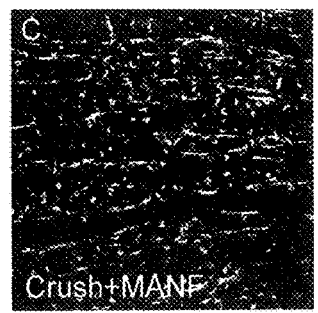

The results illustrated in FIG. 7A-C show the ability of MANF to protect retinal ganglion cells following an optic nerve crush. As shown in FIG. 7A, retralabeled ganglion cells are distributed throughout the representative micrograph in control mice. As shown in FIG. 7B, retralabeled ganglion cells are mostly degenerated two weeks after optic nerve crush in PBS-treated retinas (control). On the contrary, MANF treatment, as shown in FIG. 7C, is able to rescue many of the retinal ganglion cells two weeks following optic nerve crush and treatment.

Figure 8:
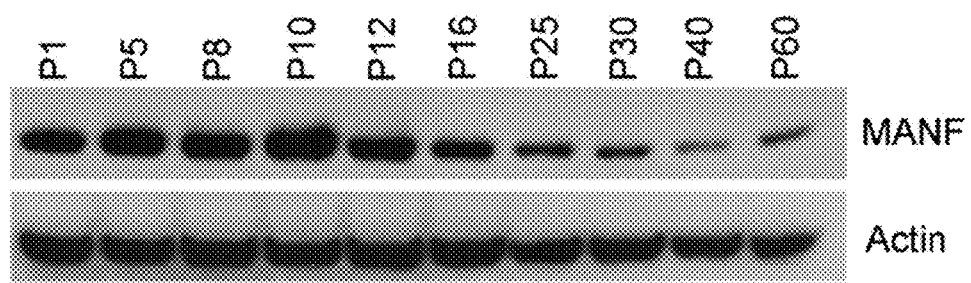
FIG. 8 shows a photograph of a Western blot probed for MANF and β-Actin (loading control). MANF expression levels in extracts from retinas of wild-type Sprague Dawley rats at PD 1, PD 5, PD 8, PD 10, PD 12, PD 16, PD 25, PD 30, PD 40 and PD 60 are shown.

Example 8: MANF Protein Expression in the Retina is Higher During Development of Photoreceptors in Rats Protein extracts from retinas of wild-type Sprague Dawley rats at PD 1, PD 5, PD 8, PD 10, PD 12, PD 16, PD 25, PD 30, PD 40 and PD 60 were analyzed by Western blot analysis for MANF expression levels. As shown in FIG. 8, high levels of MANF expression were detected during postnatal development (from PD 1 to PD 16). As the retinas mature past PD 16, the expression decreases (see the continued expression level decrease from PD 25 to PD 60 in FIG. 8).

Example 9: MANF Immunoactivity on the Retina

Figure 9:
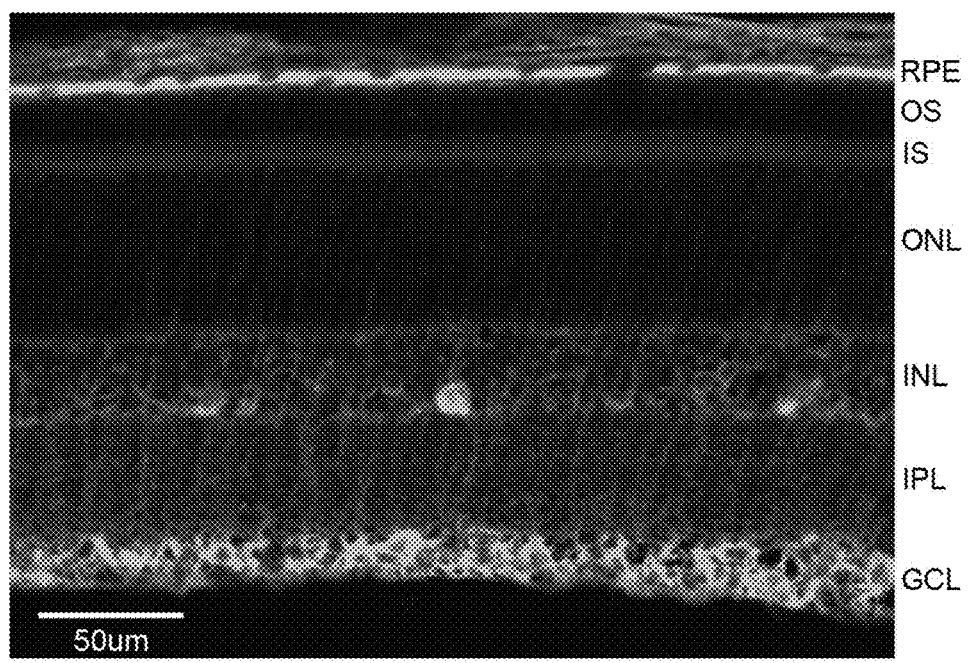
FIG. 9 shows a fluorescent microscopy photograph of a cryosection of rat retina probed with anti-MANF antibodies. Scale bar, 50 μm. Layers labeled on the section include the retinal pigment epithelium (RPE), the outer photoreceptor segment (OS), the inner photoreceptor segment (IS), the outer nuclear layer (ONL), the inner nuclear layer (INL), the inner plexiform layer (IPL), and the ganglion cell layer (GCL). The immunoactivity of MANF is shown in the RPE cells, Müller cell fibers and cell bodies, as well as in the GCL.

As shown in FIG. 9, cryosections probed with anti-MANF antibodies demonstrated that immunoactivity of MANF was located in the retinal pigment epithelium (RPE) cells, Müller cell fibers and cell bodies, as well as in the retinal ganglion cell layer.

Together, the results presented in the Examples reveal that MANF and CDNF have neuroprotective properties for photoreceptors, and at least MANF additionally has neuroprotective properties in retinal ganglion cells. Additionally, at least MANF has a high expression level during development of photoreceptors, and its level decreases as photoreceptors mature. These results suggest MANF and CDNF are therapeutic agents for retinal degenerative disorders.

It is to be appreciated that the Detailed Description section, and not the Abstract section, is intended to be used to interpret the claims. The Abstract section may set forth one or more but not all exemplary embodiments of the present invention as contemplated by the inventor(s), and thus, are not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

REFERENCES

Airavaara, M., Shen, H., Kuo, C., Peranen, J., Saarma, M., Hoffer, B. and Wang, Y. (2009). Mesencephalic astrocyte-derived neurotrophic factor reduces ischemic brain injury and promotes behavioral recovery in rats. *Journal of Comparative Neurology* 515:116-124.

Lindholm, P., Voutilainen, M. H., Lauren, J., Peranen, J., Leppanen, V., Andressoo, J., Lindahl, M., Janhunen, S., Kalkkinen, N., Timmusk, T., Tuominen, R. K. and Saarma, M. (2007). Novel neurotrophic factor CDNF protects and rescues midbrain dopamine neurons in vivo. *Nature* 448:73-78.

Liu, C., Li, Y., Peng, M., Laties, A. M. and Wen, R. (1999). Activation of caspase-3 in the retina of transgenic rats with the rhodopsin mutation S334ter during photoreceptor degeneration. *Journal of Neuroscience* 19:4778-4785.

Parkash, V., Lindholm, P., Peranen, J., Kalkkinen, N., Oksanen, E., Saarma, M., Leppanen, V. and Goldman, A. (2009). The structure of the conserved neurotrophic factors MANF and CDNF explains why they are bifunctional. *Protein Engineering, Design & Selection* 22:233-241.

Parkash, V. (2009). Neurotrophic factors and their receptors. Dissertation. University of Helsinki. Helsinki University Press.

Petrova, P. S., Raibekas, A., Pevsner, J., Vigo, N., Anafi, M., Moore, M. K., Peaire, A. E., Shridhar, V., Smith, D. I., Kelly, J., Durocher, Y. and Commissiong, J. W. (2003). A new mesencephalic, astrocyte-derived neurotrophic factor with selectivity for dopaminergic neurons. *Journal of Molecular Neuroscience* 20:173-187.

Sieving, P. A., Caruso, R. C., Tao, W. Coleman, H. R., Thompson, D. J. S., Fullmer, K. R., and Bush, R. A. (2006). Ciliary neurotrophic factor (CNTF) for human retinal degeneration: Phase I trial of CNTF delivered by encapsulated cell intraocular implants. *Proceedings of the National Academy of Science* 103: 3896-3901.

Tadimalla, A., Belmont, P. J., Thuerauf, D. J., Glassy, M. S., Martindale, J. J., Gude, N., Sussman, M. A. and Glembotski, C. C. (2008). Mesencephalic astrocyte-derived neurotrophic factor is an ischemia-inducible secreted endoplasmic reticulum stress response protein in the heart. *Circulation Research* 103:1249-1258.

Tao, W., Wen, R., Aguirre, G. D., Laties, A. M. (2006). Cell-Based delivery systems: development of encapsulated cell technology for ophthalmic applications. In G. J. Jaffe, P. Ashton (Eds.), *Intraocular drug delivery: principles and clinical applications* (Ch. 8). Taylor & Francis.

Tao, W. and Wen, R. (2007). Application of Encapsulated Cell Technology for Retinal Degenerative Diseases. In J. Tombran-Tink & C. J. Barnstable (Eds.), *Ophthalmology Research: Retinal Degenerations: Biology, Diagnostics, and Therapeutics* (401-413). New Jersey: Humana Press, Inc.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method of treating a retinal disorder selected from the group consisting of retinitis pigmentosa, age-related macular degeneration, and glaucoma, said method comprising administering an effective amount of mesencephalic astrocyte-derived neurotrophic factor (MANF) to a subject with said retinal disorder, wherein said MANF is a recombinant protein having an amino acid sequence consisting of SEQ ID NO: 3 or a c-terminal fragment of SEQ ID NO: 3 that is at least 85% the length of SEQ ID NO:3; said MANF being in saline solution, a pharmaceutically acceptable carrier.

2. The method of claim 1, wherein said retinal disorder is retinitis pigmentosa.

3. The method of claim 1, further comprising administering an effective amount of conserved dopamine neurotrophic factor (CNDF), wherein said CDNF has an amino acid sequence consisting of SEQ ID NO: 4 or a c-terminal fragment of SEQ ID NO: 4 that is at least 85% the length of SEQ ID NO:4.

4. The method of claim 1, wherein said MANF is administered to an eye of said subject.

5. The method of claim 4, wherein administering occurs by topical administration.

6. The method of claim 5, wherein said topical administration is with an eye drop.

7. The method of claim 4, wherein administering occurs by injection.

8. The method of claim 7, wherein said injection is an intravitreal injection.

9. The method of claim 1, wherein said MANF is administered in an area adjacent to the eye.

10. The method of claim 1, wherein said retinal disorder is age-related macular degeneration.

11. The method of claim 1, wherein said retinal disorder is glaucoma.

12. The method of claim 1, wherein said MANF has said amino acid sequence consisting of SEQ ID NO: 3.

13. The method of claim 1, wherein said MANF has said amino acid sequence consisting of said c-terminal fragment of SEQ ID NO: 3 that is at least 85% the length of SEQ ID NO:3.

14. A method for promoting neuroprotection in a neuronal cell, comprising contacting said neuronal cell with a neurotrophic factor comprising conserved dopamine neurotrophic factor (CNDF) and mesencephalic astrocyte-derived neurotrophic factor (MANF); wherein said neuronal cell is selected from the group consisting of a retinal ganglion cell and a photoreceptor cell, wherein said MANF has an amino acid sequence consisting a c-terminal fragment of SEQ ID NO: 3 that is at least 85% the length of SEQ ID NO:3, and wherein said CDNF has an amino acid sequence consisting of a c-terminal fragment of SEQ ID NO: 4 that is at least 85% the length of SEQ ID NO:4.

15. The method of claim 14, wherein said contacting occurs in vivo.

16. The method of claim 14, wherein said contacting occurs in vitro.

17. The method of claim 14, wherein said neuronal cell is said retinal ganglion cell.

18. The method of claim 14, wherein said neuronal cell is said photoreceptor cell.

19. The method of claim 14, wherein said neurotrophic factor is a recombinant neurotrophic factor.

20. The method of claim 14, wherein said neurotrophic factor is a human neurotrophic factor.

21. The method of claim 20, wherein said human neurotrophic factor is a recombinant human neurotrophic factor.

22. A method of treating a retinal disorder selected from the group consisting of retinitis pigmentosa, age-related macular degeneration, and glaucoma, said method comprising administering an effective amount of conserved dopamine neurotrophic factor (CNDF) to a subject with said retinal disorder; wherein said CDNF is a recombinant protein having an amino acid sequence consisting of SEQ ID NO: 4 that is at least 85% the length of SEQ ID NO:4; said CDNF being in a saline solution, a pharmaceutically acceptable carrier.

23. The method of claim 22, wherein said retinal disorder is retinitis pigmentosa.

24. The method of claim 22, wherein said CDNF is administered to an eye of said subject.

25. The method of claim 24, wherein administering occurs by topical administration.

26. The method of claim 25, wherein said topical administration is with an eye drop.

27. The method of claim 24, wherein administering occurs by injection.

28. The method of claim 27, wherein said injection is an intravitreal injection.

29. The method of claim 22, wherein said CDNF is administered in an area adjacent to the eye.

30. The method of claim 22, wherein said retinal disorder is age-related macular degeneration.

31. The method of claim 22, wherein said retinal disorder is glaucoma.

* * * * *

SEQUENCE LISTING

<160> NUMBER OF SEQ ID NOS: 4

<210> SEQ ID NO 1
<211> LENGTH: 549
<212> TYPE: DNA
<213> ORGANISM: Homo sapiens

<400> SEQUENCE: 1

```
atgaggagga tgtgggccac gcaggggctg gcggtggcgc tggctctgag cgtgctgccg      60
ggcagccggg cgctgcggcc gggcgactgc gaagtttgta tttcttatct gggaagattt     120
taccaggacc tcaaagacag agatgtcaca ttctcaccag ccactattga aaacgaactt     180
ataaagttct gccgggaagc aagaggcaaa gagaatcggt tgtgctacta tatcggggcc     240
acagatgatg cagccaccaa aatcatcaat gaggtatcaa agcctctggc ccaccacatc     300
cctgtggaga agatctgtga gaagcttaag aagaaggaca gccagatatg tgagcttaag     360
tatgacaagc agatcgacct gagcacagtg gacctgaaga agctccgagt taaagagctg     420
aagaagattc tggatgactg gggggagaca tgcaaaggct gtgcagaaaa gtctgactac     480
atccggaaga taaatgaact gatgcctaaa tatgccccca aggcagccag tgcacggacc     540
gatttgtag                                                             549
```

<210> SEQ ID NO 2
<211> LENGTH: 564
<212> TYPE: DNA
<213> ORGANISM: Homo sapiens

<400> SEQUENCE: 2

```
atgtggtgcg cgagcccagt tgctgtggtg gccttttgcg ccgggctttt ggtctctcac      60
ccggtgctga cgcagggcca ggaggccggg gggcggccag gggccgactg tgaagtatgt     120
aaagaattct tgaaccgatt ctacaagtca ctgatagaca gaggagttaa cttttcgctg     180
gacactatag agaaagaatt gatcagtttt tgcttggaca ccaaaggaaa agaaaaccgc     240
ctgtgctatt atctaggagc cacaaaagac gcagccacaa agatcctaag tgaagtcact     300
cgcccaatga gtgtgcatat gcctgcaatg aagatttgtg agaagctgaa gaagttggat     360
agccagatct gtgagctgaa atatgaaaaa acactggact tggcatcagt tgacctgcgg     420
```

```
aagatgagag tggcagagct gaagcagatc ctgcatagct ggggggagga gtgcagggcc    480
tgtgcagaaa aaactgacta tgtgaatctc attcaagagc tggcccccaa gtatgcagcg    540
acacacccca aaacagagct ctga                                           564
```

<210> SEQ ID NO 3
<211> LENGTH: 182
<212> TYPE: PRT
<213> ORGANISM: Homo sapiens

<400> SEQUENCE: 3

```
Met Arg Arg Met Trp Ala Thr Gln Gly Leu Ala Val Ala Leu Ala Leu
1               5                   10                  15

Ser Val Leu Pro Gly Ser Arg Ala Leu Arg Pro Gly Asp Cys Glu Val
            20                  25                  30

Cys Ile Ser Tyr Leu Gly Arg Phe Tyr Gln Asp Leu Lys Asp Arg Asp
        35                  40                  45

Val Thr Phe Ser Pro Ala Thr Ile Glu Asn Glu Leu Ile Lys Phe Cys
    50                  55                  60

Arg Glu Ala Arg Gly Lys Glu Asn Arg Leu Cys Tyr Tyr Ile Gly Ala
65                  70                  75                  80

Thr Asp Asp Ala Ala Thr Lys Ile Ile Asn Glu Val Ser Lys Pro Leu
                85                  90                  95

Ala His His Ile Pro Val Glu Lys Ile Cys Glu Lys Leu Lys Lys Lys
            100                 105                 110

Asp Ser Gln Ile Cys Glu Leu Lys Tyr Asp Lys Gln Ile Asp Leu Ser
        115                 120                 125

Thr Val Asp Leu Lys Lys Leu Arg Val Lys Glu Leu Lys Lys Ile Leu
    130                 135                 140

Asp Asp Trp Gly Glu Thr Cys Lys Gly Cys Ala Glu Lys Ser Asp Tyr
145                 150                 155                 160

Ile Arg Lys Ile Asn Glu Leu Met Pro Lys Tyr Ala Pro Lys Ala Ala
                165                 170                 175

Ser Ala Arg Thr Asp Leu
            180
```

<210> SEQ ID NO 4
<211> LENGTH: 187
<212> TYPE: PRT
<213> ORGANISM: Homo sapiens

<400> SEQUENCE: 4

```
Met Trp Cys Ala Ser Pro Val Ala Val Val Ala Phe Cys Ala Gly Leu
1               5                   10                  15

Leu Val Ser His Pro Val Leu Thr Gln Gly Gln Glu Ala Gly Gly Arg
            20                  25                  30

Pro Gly Ala Asp Cys Glu Val Cys Lys Glu Phe Leu Asn Arg Phe Tyr
        35                  40                  45

Lys Ser Leu Ile Asp Arg Gly Val Asn Phe Ser Leu Asp Thr Ile Glu
    50                  55                  60

Lys Glu Leu Ile Ser Phe Cys Leu Asp Thr Lys Gly Lys Glu Asn Arg
65                  70                  75                  80

Leu Cys Tyr Tyr Leu Gly Ala Thr Lys Asp Ala Ala Thr Lys Ile Leu
                85                  90                  95

Ser Glu Val Thr Arg Pro Met Ser Val His Met Pro Ala Met Lys Ile
            100                 105                 110
```

```
Cys Glu Lys Leu Lys Lys Leu Asp Ser Gln Ile Cys Glu Leu Lys Tyr
        115                 120                 125

Glu Lys Thr Leu Asp Leu Ala Ser Val Asp Leu Arg Lys Met Arg Val
        130                 135                 140

Ala Glu Leu Lys Gln Ile Leu His Ser Trp Gly Glu Glu Cys Arg Ala
145             150                 155                 160

Cys Ala Glu Lys Thr Asp Tyr Val Asn Leu Ile Gln Glu Leu Ala Pro
            165                 170                 175

Lys Tyr Ala Ala Thr His Pro Lys Thr Glu Leu
            180                 185
```